United States Patent [19]

Gebott et al.

[11] Patent Number: 4,668,363

[45] Date of Patent: May 26, 1987

[54] IMMUNOFIXATION ELECTROPHORESIS PROCESS

[75] Inventors: Michael D. Gebott, Yorba Linda; William A. Gurske, Placentia; Joan A. Macy, Huntington Beach, all of Calif.

[73] Assignee: Beckman Instruments, Inc., Fullerton, Calif.

[21] Appl. No.: 590,390

[22] Filed: Mar. 16, 1984

[51] Int. Cl.$^4$ .............................................. B01K 5/00
[52] U.S. Cl. .................................. 204/182.8; 436/516
[58] Field of Search ............ 204/182.8, 182.7, 180 G, 204/299 R; 436/516

[56] References Cited

U.S. PATENT DOCUMENTS

| | | | |
|---|---|---|---|
| 3,378,481 | 4/1968 | Saravis et al. | 204/299 R |
| 3,432,424 | 3/1969 | Zec | 204/299 R |
| 3,482,943 | 12/1969 | Csizmas et al. | 204/299 R X |
| 3,553,067 | 1/1971 | Dwyer et al. | 204/182.7 X |
| 3,912,610 | 10/1975 | Lou | 436/516 X |
| 3,932,229 | 1/1976 | Grandine | 204/299 R X |
| 4,094,759 | 6/1978 | Ruhenstroth-Baur | 204/180 |
| 4,147,606 | 4/1979 | Golias | 204/299 EC X |
| 4,312,727 | 1/1982 | Shainoff | 204/182.8 |
| 4,337,131 | 6/1982 | Vesterberg | 204/182.8 |
| 4,559,120 | 12/1985 | Royse et al. | 204/182.8 |

FOREIGN PATENT DOCUMENTS 109954  8/1980  Japan ............................. 204/180 G

OTHER PUBLICATIONS

Crowle, A. J., et al., "Microimmunoelectrophoresis: Comparison of Template with Nontemplate Methods", *J. Lab. & Clin. Med.*, vol. 59, No. 4, pp. 697–704 (1962).
Deyl, Z., *Electrophoresis*; Part A, Elsevier Scientific Publishing Co., New York, 1979, p. 128.
"Isobel System; Methodology for Agrose Isoelectric Focusing Immunofixation, and Related Techniques", FMC Product Brochure, p. 2, 1982.
Emidio Afonso, "Quantitative Immunoelectrophoresis of Serum Proteins", *Clin. Chem. Acta.*, 10(1964) 114–122.
Chester A. Alper, "Genetic Polymorphism of Complement Components as a Probe of Structure and Function", *Progress in Immunology*, First International Congress of Immunology, Acadmic Press, New York, (1971), 609–624.
A. Myron Johnson, "Genetic Typing of $\alpha_1$-Antitrypsin by Immunofixation Electrophoresis" *J. Lab. Clin. Med.*, Jan. 1976, 152–163.
Leo P. Cawley, et al., "Immunofixation Electrophoretic Techniques Applied to Identification of Proteins in Serum and Cerebrospinal Fluid", *Clinical Chemistry*, vol. 22, No. 8, 1976, 1262–1268.
Robert F. Ritchie et al., "Immunofixation. III. Application to the Study of Monoclonal Proteins, Clin. Chem., 22:12, 1982–1985 (1976).
Leo P. Cawley, "Electrophoresis and Immunoelectrophoresis", First Ed., Little, Brown and Company, Boston, pp. 235–239 (1969).
Joseph J. Cavallaro, et al., "Immunofixation Electrophoresis", U.S. Dept. of Health and Human Services, Dec. 1981.
C. A. Alper et al., "Immunofixation Electrophoresis: A Technique for the Study of Protein Polymorphism", Vox Sanguinis, 17:445–452 (1969).
Tsieh Sun, et al., "Study of Gammopathies with Immunofixation Electrophoresis", A.J.C.P., vol. 72, No. 1, Jul. 1978, pp. 5–11.
Robert F. Ritchie et al., "Immunofixation I. General Principles and Application to Agarose Gel Electrophoresis", Clinical Chemistry, vol. 22, No. 4, 1976.
Burke et al., Clin. Chem., 29(6):1174, Abstract No. 94 (1983).
Chemical Abstracts, 89(25): 270, Abstract No. 211487q.

*Primary Examiner*—John F. Niebling
*Attorney, Agent, or Firm*—W. H. May; Arnold Grant; Julia E. Abers

[57] ABSTRACT

A method comprising (a) applying a sample to at least two application areas on an electrophoretic gel; (b) electrophoresing the gel; (c) aligning a template onto the electrophoresed gel, the template having a template slot corresponding to each electrophoresed area; (d) applying a composition capable of fixing proteins in situ to at least one template slot and applying an antisera capable of reacting with one protein to at least one of the remaining template slots; (e) incubating the resultant product of step (d); (f) removing the template from the incubated, electrophoresed gel; (g) washing the incubated electrophoresed gel of step (f); (h) drying the washed gel of step (g); (i) staining the dryed gel of step (h); (j) destaining the stained gel of step (i); (k) drying the destained gel of step (j); and (l) analyzing the dryed gel of step (k).

29 Claims, No Drawings

IMMUNOFIXATION ELECTROPHORESIS PROCESS

BACKGROUND OF THE INVENTION

1. Field of the Invention

The instant invention pertains to an immunofixation electrophoresis technique.

2. Description of the Prior Art

Immunofixation electrophoresis (IFE) is a two stage procedure using agarose gel protein electrophoresis in the first stage and immunoprecipitation in the second. The specimen may be serum, urine or cerebral spinal fluid. There are numerous applications for IFE in research, forensic medicine, genetic studies and clinical laboratory procedures. The greatest demand for immunofixation electrophoresis is in the clinical laboratory where it is primarily used for the detection and identification of immunoglobulins involved in monoclonal gammopathies.

Alfonso (1) first described immunofixation in the literature in 1964. Alper et al. (2) published a more practical procedure in 1969 as a result of their work devoted to the detection of genetic polymorphisms of ceruloplasmin and Gc-globulin and the conversion of C3 during activation. They later extended their studies to genetic polymorphisms of complement components and the identification of alpha₁ antitrypsin phenotypes (3,4). Immunofixation was first introduced as a procedure for the study of immunoglobulins in 1976 (5,6). There are numerous other references pertaining to the immunofixation procedure (e.g., 7-10).

The most sophisticated immunofixation electrophoresis procedure at present involves applying a sample to several application sites on an electrophoretic gel; electrophoresing the gel; severing the protein pattern portion from the remaining portion of the gel; fixing the proteins in this severed portion of the electrophoretic gel; applying distinct antiserum to the remaining electrophoresed portions present on the gel and incubating the resulting gel; washing the incubated gel; drying the washed gel; staining the dryed gel; destaining the stained gel; drying the destained gel; and analyzing the dryed gel.

One drawback to this procedure is that the severed fixed protein portion of the gel could be misplaced or lost in addition to the inconvenience involved in initially severing the protein portion from the remainder part of the gel.

Accordingly, it would be very advantageous to have an immunofixation electrophoresis procedure wherein the protein portion of the gel need not be separated from the gel prior to the fixation of the proteins therein.

SUMMARY OF THE INVENTION

In accordance with the present invention, there is provided an improved immunofixation electrophoresis procedure wherein the protein pattern may be stained within the electrophoretic gel without the need to sever the protein precipitation pattern portion of the gel from the remaining portion thereof. More particularly, the immunofixation electrophoresis process of the instant invention comprises (a) applying a sample to at least two application areas on an electrophoretic gel; (b) electrophoresing the gel; (c) aligning a template onto the electrophoresed gel, the template having a template slot corresponding to each electrophoresed area; (d) applying a composition capable of fixing proteins in situ to at least one template slot and applying an antiserum capable of reacting with one protein to at least one of the remaining template slots; (e) incubating the resultant product of the step (d); (f) removing the template from the incubated, electrophoresed gel; (g) washing the incubated, electrophoresed gel of step (f); (h) drying the washed gel of step (g); (i) staining the dryed gel of step (h); (j) destaining the stained gel of step (i); (k) drying the destained gel of step (j); and (l) analyzing the dryed gel of step (k).

Still other features and attendant advantages of the present invention will become apparent to those skilled in the art from a reading of the following detailed description of the preferred embodiments.

DESCRIPTION OF THE PREFERRED EMBODIMENT

Polysaccharides which can preferably be employed in the electrotrophoretic gel of the instant invention are agar and agarose. The agarose can be either low electroendoosmosis agarose, medium electroendoosmosis agarose, or high electroendoosmis agarose. More preferably, the polysaccharide employed in the electrophoretic gel of the instant invention is a low electroendoosmosis agarose.

Preferably, the sample to be analyzed is applied to at least six application areas and each of at least five different antisera is individually applied to a separate electrophoresed area of the gel via each corresponding template slot. The antisera is preferably the Ig fraction of the antisera and, more preferably, is the IgG fraction of the antisera. It is also preferred that the antisera be anti-human antisera and that the anti-human antisera be IgG, IgA, IgM, Kappa, and Lambda.

The composition which is capable of fixing proteins in situ preferably comprises from about 10 to about 500, more preferably, from about 25 to about 75, g/L sulfosalicylic acid.

This composition can optionally comprise enhancing amounts of an acid having a pKa of less than or equal to about 4. Preferably, the composition comprises up to about 100, more preferably from about 10 to about 100, and optimally from about 25 to about 75, ml/l glacial acetic acid.

The following examples are provided for the purpose of further illustration only and are not intended to be limitations on the disclosed invention.

EXAMPLES 1-8

The following procedures were employed in conjunction with each protein precipitating reagent set forth in Table I.

TABLE I

| Example | Sulfosalicyclic Acid, % wt. | Glacial Acetic Acid, % wt. |
|---------|-----------------------------|----------------------------|
| 1 | 1 | — |
| 2 | 2 | — |
| 3 | 5 | — |
| 4 | 10 | — |
| 5 | 50 | — |
| 6 | 2 | 1 |
| 7 | 5 | 5 |
| 8 | 10 | 10 |

A. Electrophoretic Procedure

A1. Fill each side of the electrophoretic cell with 45 milliliters of 0.05μ barbital buffer pH 8.6.

A2. Remove an immunofixation electrophoresis (IFE) gel from the package and blot gently with a sheet of filter paper. Discard filter paper.

A3. Align a sample template on gel.

A4. Apply three to five microliters of a 1/10 dilution of test specimen to each template slot. For a serum protein electrophoresis (SPE) reference pattern, slot 1 should be a ½ dilution.

A5. Allow five minutes diffusion time after the last sample has been applied, then gently blot the template with a blotter. Discard the blotter. Remove and discard the template.

A6. Place gel onto gel bridge and into electrophoretic cell. Cover and connect to a power supply.

A7. Electrophorese at 100 volts for 30 minutes.

A8. Upon completion of electrophoresis, remove gel from the electrophoresis cell and gently blot gel with a sheet of filter paper. Discard the paper.

B. Immunofixation Procedure

B1. Align IFE antiserum template with gel. Gently rub troughs to ensure complete seal between template gel surface.

B2. Apply 80 microliters of antiserum to each antiserum trough and apply 80 microliters of a protein precipitating reagent set forth in Table I to the SPE reference trough. Avoid spillage over troughs. Do not touch gel surface with the pipet or syringe tip.

B3. Place gel in plastic tray. Cover and incubate at 45° C. for 30 minutes.

C. Staining and Drying Procedure

C1. Fill the four plastic trays with the following solutions, in the order indicated:
Saline solution, 0.85%
8-Amino-7-(3-nitrophenylazo)-2-(phenylazo)-1-napththol-3,6-disulfonic acid disodium salt protein stain, 0.5% wt/v in 5% aqueous acetic acid C2. Following incubation, remove gel from the incubation tray and remove IFE antiserum template.

C3. Place the gel into saline solution and agitate continuously for one minute.

C4. Place the gel in fresh saline solution for ten minutes.

C5. Remove gel from the saline solution.

C6. Place the gel on a flat surface and one sheet of filter paper, moistened with saline, on the gel surface, followed by two thick paper blotters. Place a flat 5 lb. weight over the assembly. Press for ten minutes.

C7. Remove the gel from the press arrangement and repeat saline wash with fresh saline and press (C4, C5 and C6).

C8. After the second press, place gel into dryer for three minutes or until completely dry.

C9. Place gel into 8-Amino-7-(3-nitrophenylazo)-2-(phenylazo)-1-napththol-3,6-disulfonic acid disodium salt protein stain for three to five minutes.

C10. Remove gel from stain solution and place in acetic acid solution for two minutes.

C11. Remove gel from first acetic acid solution and place into second acetic acid solution for two minutes, or until background is clear.

C12. Remove gel from final acetic acid solution, rinse in deionized water and place in dryer for five minutes or until dry.

By applying each of the protein precipitation reagents of Table I to a localized area of the gel via a template method, only the proteins located in a small area of the gel were precipitated thus allowing the rest of the gel area to be processed by an immunofixation technique. Accordingly, this invention enables one to obtain a reference pattern on the same gel for comparison with the immunofixation patterns.

In contrast, prior art techniques fix proteins in the gel by completely immersing the total gel in a protein precipitation reagent, such as acetic acid in methyl alcohol. Such prior art techniques require the severance of the protein electrophoresed pattern prior to such immersion in order to avoid also fixing the remaining electrophoresed areas.

Based on this disclosure, many other modifications and ramifications will naturally suggest themselves to those skilled in the art. These are intended to be within the scope of this invention.

Bibliography

1. Alfonso, *Clin. Chem Acta,* 10:114–122 (1964).
2. Alper et al., Vo Sang 17:445–452 (1969).
3. Alper, *Progress in Immunology, First International Congress of Immunology,* Amos, Editor, Academic Press, NY, NY pp. 609–624 (1971).
4. Johnson, *J. Lab. Clin. Med.,* 87:152–163 (1976).
5. Cawley et al., *Clin. Chem.,* 22:1262–1268 (1976).
6. Ritchie et al., *Clin. Chem.,* 22:1982–1984 (1976).
7. Cawley, *Electrophoresis and Immunoelectrophoresis,* 1st Edition, Little, Brown, and Co., Boston, MA (1969).
8. Cavallaro et al., *Immunofixation Electrophoresis,* U.S. Dept. of Health and Human Services, Atlanta, GA (1981).
9. Sun et al., *A.J.C.P.,* 72(1):5–11 (1979).
10. Ritchie et al., *Clin. Chem.,* 22(4):497–499 (1976).

The embodiments of the invention in which an exclusive property or provilege is claimed are defined as follows:

1. An electrophoresis method comprising:
   (a) applying a sample to at leat two application areas on an electrophoretic gel;
   (b) electrophoresing said gel to obtain electrophoresis protein patterns in said gel;
   (c) aligning a template onto the electrophoresed gel, the template having a template slot corresponding to each electrophoresed area;
   (d) applying a composition capable of fixing proteins in said gel in situ without severing protein patterns of said gel before application through a template slot and applying an antiserum capable o reacting with a protein through another template slot;
   (e) incubating the resultant product of step (d);
   (f) removing the template from the incubated; electrophoresed gel;
   (g) washing the incubated electrophresed gel of step (f);
   (h) drying the washed gel of step (g);
   (i) staining the dryed gel of step (h);
   (j) destaining the stained gel of step (i);
   (k) drying the destained gel of step (j); and
   (l) analyzing the dryed gel of step (k).

2. The method of claim 1 wherein said antisera are the Ig fraction of the antisera.

3. The method of claim 1 wherein said antisera are the IgG fraction of the antisera.

4. The method of claimm 1 wherein said antisera are anti-human antisera.

5. The method of claim 4 wherein said anti-human antisera are the Ig fraction fothe antisera and aid anti-human antisera are IgG, IgA, IgM, Kappa, and Lambda.

6. The method of claim 4 wherein said anti-human antisera are the IgG fraction of the antisera and said anti-human antisera are IgG, IgA, IgM, Kappa, and Lambda.

7. The method of claim 1 wherein said composition comprises from about 10 to about 500 g/l sulfosalicyclic acid.

8. The method of claim 7 wherein said composition further comprises an enhancing amount of an acid having a pKa of less than or equal to 4.

9. The method of claim 1 wherein said composition comprises from about 10 to about 500 g/L sulfosalicyclic acid and up to about 100 ml/L glacial acetic acid.

10. The method of claim 9 wherein said composition comprises from about 25 to about 75 g/L sulfosalicyclic acid and from about 25 to about 75 ml/L glacial acetic acid.

11. The method of claim 10 wherein said antisera are the Ig fraction of the antisera.

12. The method of claim 10 wherein said antisera are the IgG fraction of the antisera.

13. The method of claim 10 wherein said antisera are anti-human antisera.

14. The method of claim 13 wherein said anti-human antisera are Ig fraction oF the antisera and said anti-human antisera are IgG, IgA, IgM, Kappa, and Lambda.

15. The method of claim 13 wherein said anti-human antisera are the IgG fraction of the antisera and said anti-human antisera are IgG, IgA, IgM, Kappa, and Lambda.

16. An electrophoresis method comprising:
    (a) applying a sample to at least two application areas on an electrophoretic gel;
    (b) electrophroesing said gel to obtain electrophoresis protein patterns in said gel;
    (c) alinging a template onto the electrophoresed gel, the template having a template slot corresponding to each electrophoresed area;
    (d) applying a composition capable of fixing proteins in said gel in situ without severing protein patterns of said gel before application through a template slot and applying an antiserum capable of reacting with a protein through another template slot; and,
    (e) incubating the resultant product of step (d).

17. The method of claim 16 wherein sand antisera are the Ig fraction of the antisera.

18. The method of claim 16 wherein said antisera are the IgG fraction of the antisera.

19. The method of claim 16 wherein said antisera are anti-human antisera.

20. The method of claim 16 wherein said anti-human antisera are the Ig fraction of the antisera and said anti-human antisera are IgG, IgA, Kappa, and Lambda.

21. The method of claim 16 wherein said anti-human antisera are the IgG fraction of the antisera and said anti-human antisera are IgG, IgA, IgM, Kappa, and Lambda.

22. The method of claim 16 wherein said composition comprises from about 10 to about 500 g/L sulfosalicyclic acid.

23. The method of claim 22 wherein said composition further comprises an enhancing amount of an acid having a pKa of less than or equal to 4.

24. The method of claim 23 wherein said composition comprises from about 25 to about 75 g/L sulfosalicyclic acid and from about 25 to about 75 ml/L glacial acetic acid.

25. The method of claim 24 wherein said antisera are the Ig fraction of the antisera.

26. The method of claim 24 wherein said antisera are the IgG fraction ofthe antisera.

27. The method of claim 24 wherein said antisera are anti-huamn antisra.

28. The method of claim 27 wherein said anti-human antisera are the Ig fraction Of the antisra and said anti-human antisera are IgG, IgA, IgM, Kappa, and Lambda.

29. The method of claim 27 wherein said anti-human antisera are the IgG fraction of the antisera and said anti-human antisera are IgG, IgA, IgM, Kappa, and Lambda.

* * * * *